United States Patent [19]

Pocknell

[11] Patent Number: 4,991,574
[45] Date of Patent: Feb. 12, 1991

[54] SURGICAL DRESSING

[75] Inventor: David Pocknell, Antibes, France

[73] Assignee: Dow Corning Corporation, Midland, Mich.

[21] Appl. No.: 568,539

[22] Filed: Aug. 15, 1990

Related U.S. Application Data

[63] Continuation of Ser. No. 222,445, Jul. 21, 1988, abandoned.

[30] Foreign Application Priority Data

Jul. 22, 1987 [FR] France ............................ 87 10364

[51] Int. Cl.$^5$ ............................................. A61L 15/00
[52] U.S. Cl. .................................. 128/156; 128/155; 128/DIG. 21; 424/445
[58] Field of Search ............... 128/DIG. 21, 155, 156; 604/289, 304, 307, 308; 424/443, 445, 447, 448

[56] References Cited

U.S. PATENT DOCUMENTS

| | | | |
|---|---|---|---|
| 3,020,260 | 2/1962 | Nelson | 260/46.5 |
| 3,249,109 | 5/1966 | Maeth et al. | 604/304 |
| 3,648,692 | 3/1972 | Wheeler | 128/156 |
| 3,731,683 | 5/1973 | Zaffaroni | 604/304 |
| 3,800,792 | 4/1974 | McKnight et al. | 128/156 |
| 3,949,742 | 4/1976 | Nowakowski | 128/155 |
| 4,690,683 | 9/1987 | Chien et al. | 128/156 |
| 4,762,680 | 8/1988 | Pennace et al. | 128/156 |
| 4,838,253 | 6/1989 | Brassington et al. | 604/304 |
| 4,921,074 | 5/1990 | Fabo | 128/156 |

FOREIGN PATENT DOCUMENTS 849885 9/1960 United Kingdom .
945580 1/1964 United Kingdom .

OTHER PUBLICATIONS

Perkins, K., et al., "Silicone gel: a new treatment for burn scars and contractures", *Burns*, vol. 9. No. 3, pp. 201–204.

Primary Examiner—Stephen C. Pellegrino
Assistant Examiner—Michael Rafa
Attorney, Agent, or Firm—Cargill & Associates

[57] ABSTRACT

A surgical dressing comprising a sheet of silicone gel having a wound-facing surface and laminated to the other surface a film of silicone elastomer.

The dressing is particularly adapted to the treatment of burns.

9 Claims, 1 Drawing Sheet

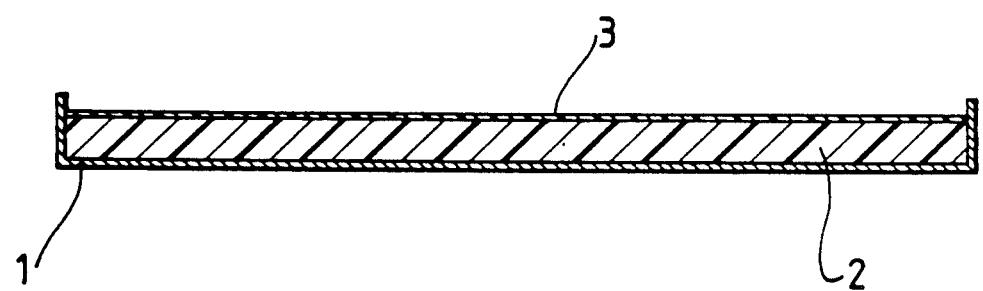

SURGICAL DRESSING

This is a continuation of co-pending application Ser. No. 07/222,445 filed on July 21, 1988, now abandoned.

This invention relates to a medical or surgical dressing suitable for use in the treatment of burns and other injury.

The treatment of severe burns involves several phases. During the healing process management of the wound involves removing exudates and providing a sterile environment in which the formation of new skin cover can take place. Various forms of dressing for assisting in such management have been proposed. For example U.S. Pat. No. 3,648,692 discloses a medical-surgical dressing for topical application to burns and the like which comprises a facing layer of neutral thrombogenic reticulated open cell material and a mutually secured co-extensive, gas-permeable microporous backing.

U.S. Pat. No. 3,800,792 discloses a surgical dressing that is particularly useful for the treatment of burn wounds and which is made from a layer of collagen compressed foam film to which has been laminated a thin continuous layer of an inert polymer material such as polyurethane.

U.S. Pat. No. 3 949,742 discloses a medical dressing which is adapted to perform as a synthetic skin for the therapy and protection of skin wounds, such as burns. The dressing comprises a unitary composite of a thin layer of thrombogenic reticulated foam cohesively secured to a thin elastomeric backing preferably of segmented polyurethane resin.

A further phase in burn therapy involves management of the burn scar. This is aimed at preventing scars from interfering with joint movement and other functions, and with reducing the cosmetic damage resulting from the scarring. A widely employed method of treating such scarring has been the use of pressure dressings. However, that method is less than satisfactory when the area to be treated is in a depression or in proximity to a joint. Another method has been described in the journal Burns, 9, pages 201-204 and involves the application of a silicone gel. Such a gel adapts itself readily to the contours of the human body and is indicated as an effective aid in the management of hypertrophic scarring.

By their nature silicone gels are difficult to handle. They are soft and frangible and the gel sheets are thus easily torn in use. It has been proposed to improve the strength and ease of handling of silicone gel sheets by embedding therein during manufacture a support material such as a net of polyester or other fibres. Although this technique has resulted in an improvement in the ability to handle and apply the gel sheet it has been found that the sheet still has a tendency to fragment during application and in use.

According to the present invention there is provided a surgical dressing comprising a sheet of silicone gel having a wound facing surface and a distal surface and a film of silicone elastomer laminated to said distal surface.

The sheet of silicone gel which forms one component of the dressing of this invention may be of any desired size. Depending on the area to be covered they may vary from a few to hundreds of square centimeters in area. The thickness of the gel layer is not critical but it should not be so thick that it will not conform substantially to the contours of the area to be covered. For general application a gel sheet having a thickness of from about 1 mm to about 6 mm is preferred. Any silicone gel-forming composition may be employed in the fabrication of the gel sheets. Such gel-forming compositions are well known and have previously been employed in the production of surgical prostheses and in the encapsulation of electronic components. They can be described as soft, tacky, non-friable gels and can be obtained by reacting a polydiorganosiloxane with a crosslinking agent and a catalyst for the crosslinking reaction. The consistency of the gel is determined by the ratio of reactive groups in the crosslinking agent to those in the polyorganosiloxane. Preferred as the gel-forming compositions are those which can be obtained by the reaction of an alkenyl-substituted polydiorganosiloxane, preferably a polydimethylsiloxane having silicon-bonded vinyl, allyl or hexenyl groups, an organosiloxane containing silicon-bonded hydrogen atoms and a catalyst for the reaction of SiH groups and silicon-bonded alkenyl groups, such catalysts usually being the platinum metals or compounds or complexes thereof. Compositions of this type may contain a small proportion of free polydiorganosiloxane fluid resulting from incomplete reaction of the alkenylsubstituted polydiorganosiloxane or from the incorporation of a non-reactive siloxane e.g. a liquid polydimethylsiloxane. They can be prepared according to the disclosures in, for example G.B. Patents 849 885, 945 580 and U.S. Pat. No. 3,020,260. Such compositions cure at normal ambient temperatures. If desired, however, curing can be expedited by exposure to elevated temperatures, e.g. from about 40° C. to about 120° C.

The silicone elastomer film which is laminated to the silicone gel sheet preferably has a thickness of from about 0.01 cm to about 0.1 cm. Thinner films can be employed but are more difficult to fabricate. Films of thickness up to about 0.2 cm are also operative but such thicker films reduce the ability of the gel sheet to conform to the body contour and offer no compensating advantage. To obtain the maximum advantage from the presence of the film of silicone elastomer it should be at least substantially co-extensive with the gel sheet. If desired the edges of the film may extend beyond the periphery of the gel sheet thus providing an area to which an adhesive may be applied for adhering the dressing to the body.

The silicone elastomer film can be fabricated from any silicone elastomer-forming composition. Basically the formation of a silicone elastomer involves the cross-linking of a polydiorganosiloxane by means of suitable techniques, for example exposure to electromagnetic radiation or, more commonly by the addition of a curing agent such as an organic peroxide or per ester and application of heat, or by the addition of a combination of a crosslinking agent e.g. an alkoxy silane or an alkylhydrogen polysiloxane, and a catalyst for the crosslinking reaction. In addition to the polydiorganosiloxane and crosslinking additives the elastomer-forming composition may contain other components such as fillers, pigments, low temperature cure inhibitors and additives for improving adhesion to the gel surface.

Preferred as the silicone elastomer-forming compositions are those based on an alkenyl-, e.g. vinyl-, substituted polydimethylsiloxane, an organosiloxane having silicon-bonded hydrogen atoms and a compound or complex of a platinum metal. Compositions of this type can be prepared in flowable form, they adhere to the silicone gel surface and can be cured at relatively low temperatures e.g. from about 30° C. to about 90° C. They are especially suitable for use according to the fabrication technique hereinafter described employing a tray or similar shallow container.

According to one method of making the dressing of this invention the gel sheet and the silicone elastomer film may be preformed by known procedures e.g. by moulding, calendering or casting and thereafter brought together. For example, the gel sheet may be preformed by casting and curing the gel-forming composition on a suitable substrate. The elastomer film may be preformed by calendering and the cured film applied over the gel sheet. Alternatively, the procedure may be reversed and the elastomer film applied first to the substrate. If necessary an adhesive may be employed to hold the components together in the laminated configuration.

Another method of making the dressings of this invention comprises (1) applying to a substrate a first composition which is a silicone gel-forming composition or is a silicone elastomer-forming composition, (2) curing the applied composition, (3) applying to the exposed surface of the cured first composition a layer of a second composition which is a silicone elastomer-forming composition or a silicone gel-forming composition respectively and (4) curing the second composition, whereby there is obtained a laminate of a silicone gel and a silicone elastomer.

In the performance of said method of this invention either the gel layer or the elastomer layer may be formed first. Thus, the first composition may be the gel-forming composition and the elastomer-forming composition is then applied as the second composition to the exposed surface of the cured gel. Alternatively, the elastomer-forming composition may be applied to the substrate as the first composition, the gel-forming composition being thereafter applied over the cured elastomer. If desired the formation of the elastomer film on the substrate may be facilitated by applying the elastomer-forming composition as a dispersion or solution in a volatile organic solvent or other carrier and thereafter removing the carrier by evaporation.

The substrate employed in step (1) of the process can be any surface which will impart to the applied compositions the desired sheet configuration. Thus, it may be a continuous belt on to which the gel-forming or elastomer-forming composition is spread. Depending on the consistency of the compositions the substrate may have barriers at its edges to restrict the flow of the compositions until cure takes place. A more preferred form of substrate, however, is a non-porous shallow container for example a tray of plastic into which the first composition is poured to a depth corresponding respectively to the desired thickness of the gel sheet or elastomeric film. The applied composition is then cured and the second composition applied to the required depth over the exposed surface of the cured first composition. Following the cure of the second composition the resulting composite, that is the gel sheet with its backing film of silicone elastomer may be removed and packaged. More conveniently, however, the composite is allowed to remain in the shallow container until ready for use.

Such an arrangement is depicted in section in the drawing wherein an imperforate gel sheet 2 has on its exposed surface an imperforate film of silicone elastomer 3. The composite dressing is contained in a shallow tray 1 from which it is removed when required for use.

The container and contents may be sterilised if necessary and enclosed in a suitable sterile envelope or other external package ready for supply and use. It will thus be appreciated that the fabrication of the gel dressing in a tray or similar shallow container, as described hereinabove, has the significant advantage of minimising the handling of the dressing during manufacture, packaging and application.

When it is desired to carry out the manufacture of the dressings of this invention as a continuous process it is generally preferred to preform the cured, silicone elastomer film as a separate operation, for example by calendering or extrusion. The preformed film is then brought into contact with the silicone gel-forming composition which is thereafter cured. Thus, for example, the cured film may be laid on the exposed surface of the gel-forming composition supported on a suitable substrate, or, alternatively the gel-forming composition may be coated on to the preformed elastomer film. Cure of the gel-forming composition is then carried out, preferably by exposure to elevated temperatures.

The surgical dressings of this invention are particularly adapted for the treatment of hypertrophic scars during burn therapy. They may also find application in earlier phases of the treatment of burns and in the treatment of wounds generally. If desired the dressings of this invention may contain or may be employed in conjunction with pharmaceutically-active substances, for example antiseptics, antibacterial agents, antifungal agents or other adjuvants employed in burn and wound treatment. Such adjuvants may be retained within the dressing or may be released during contact with the wound. Of special interest among such other adjuvants are growth factors, that is substances for increasing the rate of growth of new skin.

The following Examples illustrate the invention.

EXAMPLE 1

A silicone elastomer-forming composition was prepared based on a mixture of a vinyl-substituted polydimethylsiloxane, a polymethylhydrogensiloxane, a reinforcing silica filler and a complex of chloroplatinic acid and a vinyl siloxane as catalyst. The composition was mixed with an equal weight of trichloroethane and the resulting 50% dispersion poured into a flat rectangular plastic tray of dimensions 150 mm × 120 mm × 5 mm to a depth of 0.25 mm. The tray was placed in an oven at 50° C. for 20 minutes to evaporate the solvent and then heated to 80° C. for one hour to cure the elastomer. The tray and contents were allowed to cool and there was then poured on to the exposed surface of the cured elastomer, to a thickness of 4 mm, a flowable silicone gel-forming composition based on a similar platinum-catalysed cure system as the elastomer except that it contained no filler and the relative proportions of the vinyl groups and SiH groups were such as to provide a soft, tacky gel after cure. The tray and contents were placed in an oven at 90° C. for 20 minutes to cure the applied gel-forming composition.

When cool the tray and contents were packaged in a sealable paper pouch and sterilised by exposure to ethylene oxide.

EXAMPLE 2

A flowable, silicone elastomer-forming composition was prepared by mixing a vinyl-substituted polydimethylsiloxane, a polymethylhydrogen-siloxane, a reinforcing silica filler and a complex of chloroplatinic acid and a vinyl siloxane as catalyst. The composition was then coated on to a sheet of polyester film and its exposed surface covered with a second polyester film. The composite was passed between the rolls of calender and then exposed to a temperature of about 90° C. to effect cure of the elastomer. Upon cooling and removal of the polyester film there was obtained a silicone elastomer film having a thickness of 0.018 cm.

A portion of the film prepared as above was placed flat on the exposed surface of a layer of silicone, gel-forming composition of the type described in Example 1. The layer had a thickness of approximately 4 mm and was contained in a shallow plastic tray of dimensions 150 mm×120 mm×5 mm. The tray and contents were then placed in an oven at 90° C. for 20 minutes to effect cure of the gel-forming composition. On cooling and removal from the tray the silicone elastomer film was found to be bonded firmly to the silicone gel layer.

That which is claimed is:

1. A surgical dressing comprising an imperforate sheet of silicone gel having a wound-facing surface and a distal surface and an imperforate film of silicone elastomer substantially coextensively laminated to said distal surface.

2. A surgical dressing as claimed in claim 1 wherein the silicone gel and silicone elastomer are both derived from compositions comprising an alkenyl-substituted polydimethylsiloxane, an organosiloxane having silicon-bonded hydrogen atoms and a compound or complex of a platinum metal.

3. A surgical dressing as claimed in claim 1 which includes an antiseptic, antibacterial agent, antifungal agent or other substance employed in the treatment of wounds and burns.

4. A surgical dressing as claimed in claim 3 wherein said other substance is a growth factor.

5. A process for making a surgical dressing which comprises forming an imperforate cured silicone gel sheet and an imperforate cured silicone elastomer film and thereafter substantially coextensively laminating said film with said sheet.

6. A process for making a surgical dressing which comprises (1) applying to a non-porous substrate a first composition which is a silicone gel-forming composition or is a silicone elastomer-forming composition, (2) curing the applied composition to form an imperforate layer of cured first composition, (3) applying to the exposed surface of the cured first composition a layer of a second composition which is a silicone elastomer-forming composition or a silicone gel-forming composition respectively and (4) curing the second composition to form an imperforate layer of cured second composition, whereby there is obtained a substantially coextensive laminate of an imperforate sheet of silicone gel and an imperforate film of silicone elastomer.

7. A process as claimed in claim 6 wherein the substrate is a tray.

8. A process for making a surgical dressing which comprises contacting an imperforate, cured silicone elastomer film with a silicone gel-forming composition, thereafter curing the silicone gel-forming composition in contact with said silicone elastomer film to form an imperforate sheet of silicone gel whereby there is obtained a substantially coextensive laminate of an imperforate sheet of silicone gel and an imperforate film of silicone elastomer.

9. A process as claimed in claim 8 wherein the silicone gel and silicone elastomer are both derived from compositions comprising an alkenyl-substituted polydimethylsiloxane, an organosiloxane having silicon-bonded hydrogen atoms and a compound or complex of a platinum metal.

* * * * *